(12) United States Patent
Yates et al.

(10) Patent No.: US 10,555,748 B2
(45) Date of Patent: Feb. 11, 2020

(54) FEATURES AND METHODS TO CONTROL DELIVERY OF COOLING FLUID TO END EFFECTOR OF ULTRASONIC SURGICAL INSTRUMENT

(71) Applicant: Ethicon Endo-Surgery, LLC, Guaynabo, PR (US)

(72) Inventors: David C. Yates, West Chester, OH (US); Benjamin M. Boyd, Fairborn, OH (US); Benjamin D. Dickerson, Cincinnati, OH (US); Brian D. Black, Loveland, OH (US); Craig N. Faller, Batavia, OH (US); Kristen G. Denzinger, Cincinnati, OH (US); Paul F. Riestenberg, North Bend, OH (US); David M. Locke, Springboro, OH (US); Jacob S. Gee, Cincinnati, OH (US); Joseph Dennis, Cincinnati, OH (US); Ashvani K. Madan, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 301 days.

(21) Appl. No.: 15/163,824

(22) Filed: May 25, 2016

(65) Prior Publication Data
US 2017/0340345 A1  Nov. 30, 2017

(51) Int. Cl.
A61B 17/32 (2006.01)
A61B 17/3211 (2006.01)
A61B 17/00 (2006.01)

(52) U.S. Cl.
CPC .. *A61B 17/320068* (2013.01); *A61B 17/3211* (2013.01); *A61B 2017/00084* (2013.01);
(Continued)

(58) Field of Classification Search
CPC ........ A61B 17/320068; A61B 17/3211; A61B 2017/320084; A61B 2017/00084;
(Continued)

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

| EP | 2 572 660 A2 | 3/2013 |
| EP | 2 848 215 A1 | 3/2013 |
| JP | 2960954 B2 | 10/1999 |

OTHER PUBLICATIONS

U.S. Appl. No. 61/410,603, filed Nov. 5, 2010.
(Continued)

*Primary Examiner* — Erich G Herbermann
(74) *Attorney, Agent, or Firm* — Frost Brown Todd LLC

(57) ABSTRACT

An apparatus includes a body assembly, an acoustic waveguide, an ultrasonic blade, a liquid dispensing feature, and a control module. The liquid dispensing feature is positioned distally relative to the body assembly. The liquid dispensing feature is positioned adjacent to the ultrasonic blade. The liquid dispensing feature is configured to deliver a flow of cooling liquid to the ultrasonic blade. The control module is operable to regulate fluid flow through the liquid dispensing feature.

19 Claims, 10 Drawing Sheets

(52) U.S. Cl.
CPC ............. *A61B 2017/320084* (2013.01); *A61B 2217/007* (2013.01)

(58) Field of Classification Search
CPC .. A61B 2217/007; A61B 2017/320098; A61B 2017/00154; A61B 2017/00367; A61B 2018/00005; A61B 2018/00029; A61B 2018/00196; A61B 2018/00642; A61B 2018/00744; A61B 2018/00791; A61B 2018/00845; A61B 2218/002
See application file for complete search history.

(56) References Cited

U.S. PATENT DOCUMENTS

| | | | |
|---|---|---|---|
| 5,980,510 A | 11/1999 | Tsonton et al. | |
| 6,325,811 B1 | 12/2001 | Messerly | |
| 6,443,969 B1 | 9/2002 | Novak et al. | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,562,642 B2 | 10/2013 | Oyola et al. | |
| 8,591,459 B2 | 11/2013 | Clymer et al. | |
| 8,591,536 B2 | 11/2013 | Robertson | |
| 8,623,027 B2 | 1/2014 | Price et al. | |
| 8,961,547 B2 | 2/2015 | Dietz et al. | |
| 8,986,302 B2 | 3/2015 | Aldridge et al. | |
| 9,023,071 B2 | 5/2015 | Miller et al. | |
| 9,044,261 B2 | 6/2015 | Houser | |
| 9,381,058 B2 | 7/2016 | Houser et al. | |
| 2003/0204199 A1* | 10/2003 | Novak ........... | A61B 17/320068 606/169 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0298743 A1* | 11/2010 | Nield ............. | A61N 7/00 601/2 |
| 2012/0116265 A1 | 5/2012 | Houser et al. | |
| 2013/0072950 A1* | 3/2013 | Ross ............. | A61B 17/32 606/169 |
| 2013/0090576 A1 | 4/2013 | Stulen et al. | |
| 2015/0148832 A1 | 5/2015 | Boudreaux et al. | |
| 2016/0106455 A1 | 4/2016 | Aldridge et al. | |

OTHER PUBLICATIONS

U.S. Appl. No. 15/163,811, filed May 25, 2016.
U.S. Appl. No. 61/410,129, filed Nov. 5, 2010.
International Search Report and Written Opinion dated Jul. 25, 2017 for Application No. PCT/US2017/032626, 13 pgs.

\* cited by examiner ized Surgical Instruments," published Jan. 20, 2011, issued as U.S. Pat. No 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

FEATURES AND METHODS TO CONTROL DELIVERY OF COOLING FLUID TO END EFFECTOR OF ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issed as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Ultrasonic surgical instruments such as those described in the above-cited references may be primarily used to sever and/or seal soft tissue. However, it may be desirable to use an ultrasonic surgical instrument to cut bone, in addition to or as an alternative to cutting/sealing soft tissue. Cutting bone with an ultrasonic surgical instrument may generate more heat than cutting/sealing soft tissue with an ultrasonic surgical instrument. Unless properly addressed, this additional heat may cause undesirable effects, such as damage (e.g., necrosis) to adjacent bone and/or tissue; and/or damage to the ultrasonic blade.

Some conventional ultrasonic surgical instruments may be configured to use fluid to cool an ultrasonic blade. Examples of such instruments are described in U.S. Pub. No. 2015/0148832, entitled "Features to Apply Fluid to an Ultrasonic Blade of a Surgical Instrument," published May 28, 2015, issued as U.S. Pat. No. 10,034,658 on Jul. 31, 2018, the disclosure of which is incorporated by reference herein. Other examples of ultrasonic surgical instruments that are configured to communicate fluid are described in U.S. Pub. No. 2013/0090576, entitled "Surgical Instrument with Ultrasonic Waveguide Defining a Fluid Lumen, published Apr. 11, 2013, now abandoned, the disclosure of which is incorporated by reference herein; and U.S. Pat. No. 8,591,459, entitled "Use of Biomarkers and Therapeutic Agents with Surgical Devices," issued Nov. 26, 2013, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
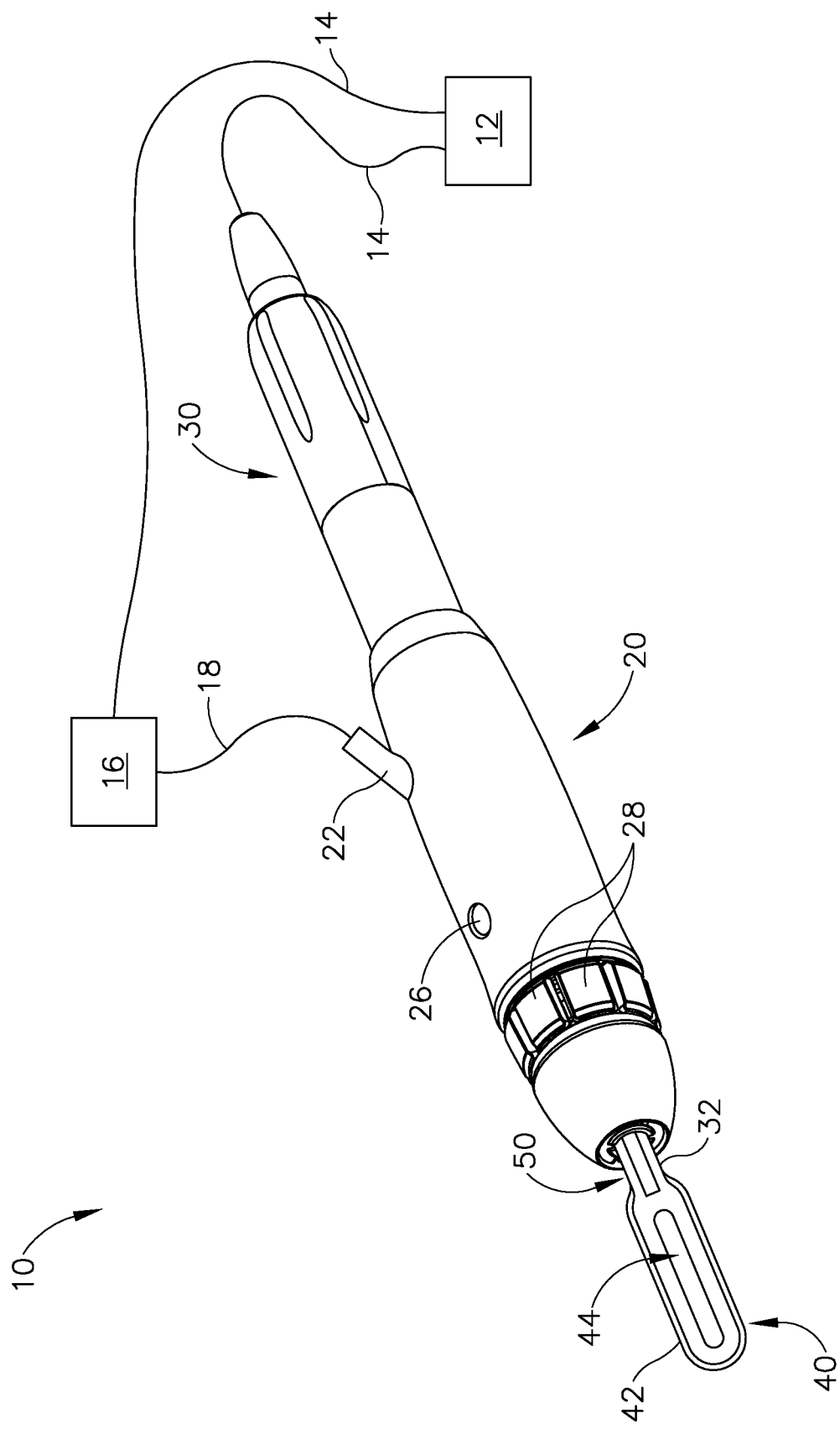
FIG. 1 depicts a perspective view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument with Generator Controlled Liquid Cooling Pump FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), an ultrasonic transducer assembly (30), an ultrasonic blade (40), and a liquid dispensing feature (50). Handle assembly (20) is configured to be grasped using a pencil grip, though some operators may choose to grasp handle assembly (20) in some other fashion (e.g., using a power grip, etc.). Handle assembly (20) includes a fluid port (22), a fluid switch (26), and a plurality of activation buttons (28).

Fluid port (22) is configured to couple with a fluid conduit (18), which is further in communication with a fluid source (16). Fluid conduit (18) may comprise a flexible tube and/or any other kind of conduit (18). By way of example only, fluid conduit (18) may be coupled with fluid port (22) via a luer fitting and/or any other suitable kind(s) of connection features. Fluid source (16) of the present example comprises a pump that is operable to pressurize a cooling liquid and thereby drive the cooling liquid toward handle assembly (20) via fluid conduit (18). Fluid source (16) is in communication with generator (12) via a cable (14). Generator (12) is operable to provide power and/or control signals to fluid source (16) via cable (14), such that generator (12) is operable to selectively activate the pump of fluid source (16) as will be described in greater detail below. It should be understood that generator (12) may thus serve as a control module.

Fluid switch (26) is operable to selectively control the flow of fluid from fluid source (16) to liquid dispensing feature (50). For instance, fluid switch (26) may be operable to actuate a valve to transition the valve between an open state and a closed state. In some other versions, fluid switch (26) is omitted and the flow of fluid from fluid source (16) to liquid dispensing feature (50) is regulated based only on the selective activation of the pump in fluid source (16) by generator (12) as will be described in greater detail below. As yet another merely illustrative example, fluid and power may both be regulated by a unit such as the CODMAN® MALTS® CMC® V generator system by Codman & Shurtleff, Inc. of Raynham, Mass. Various components and configurations that may be used to selectively restrict the flow of fluid from fluid source (16) to liquid dispensing feature

(50) will be apparent to those of ordinary skill in the art in view of the teachings herein. It should also be understood that any suitable fluids may be communicated from fluid source (16) to liquid dispensing feature (50) to cool a surgical site, including but not limited to saline.

Ultrasonic transducer assembly (30) extends proximally from handle assembly (20) and is coupled with a generator (12) via a cable (14), such that transducer assembly (30) receives electrical power from generator (12). Piezoelectric elements in transducer assembly (30) convert that electrical power into ultrasonic vibrations. Generator (12) may include a power source and control module that is configured to provide a power profile to transducer assembly (30) that is particularly suited for the generation of ultrasonic vibrations through transducer assembly (30). By way of example only, generator (12) may comprise a GEN04 or GEN11 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. In versions where generator (12) is capable of driving various different kinds of ultrasonic surgical instruments (e.g., with different resonant frequencies), handle assembly (20) may include an EEPROM or some other feature that identifies the type of ultrasonic surgical instrument (10) for generator (12), such that generator (12) may automatically select and deliver the appropriate power profile based on the identified type of ultrasonic surgical instrument (10).

It should also be understood that at least some of the functionality of generator (12) may be integrated into handle assembly (20), and that handle assembly (20) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

In the present example, transducer assembly (30) is activated in response to the operator actuating at least one button (28) of handle assembly (20). Buttons (28) are provided in an angularly spaced array about the longitudinal axis defined by handle assembly (20). The configuration and arrangement of buttons (28) in the present example enables an operator to easily access and actuate at least one button (28) regardless of the angular orientation of handle assembly (20) in the operator's hand. In other words, the operator will be able to easily actuate at least one button (28) with the thumb or index finger of the operator's hand that is grasping handle assembly (20) using a pencil grip. By way of example only, buttons (28) may be configured and operable in accordance with at least some of the teachings of U.S. patent application Ser. No. 14/515,129, entitled "Activation Features for Ultrasonic Surgical Instrument," filed Oct. 15, 2014, issued as U.S. Pat. No. 9,907,565 on Mar. 6, 2018, the disclosure of which is incorporated by reference herein. Alternatively, handle assembly (20) may have any other suitable user input features that are operable to selectively activate transducer assembly (30). As yet another merely illustrative alternative, transducer assembly (30) may be selectively activated using some other kind of user input (e.g., footswitch, etc.).

Ultrasonic blade (40) of the present example includes a sharp edge (42) extending around the outer perimeter of blade (40). Ultrasonic blade (40) also defines an oblong transverse opening (44). Ultrasonic blade (40) thus has an elongate "O" shape or hollow elliptical shape in this example, similar to the head of a sewing needle (with opening (44) being similar to the eye of a sewing needle). Ultrasonic blade (40) is acoustically coupled with ultrasonic transducer assembly (30) via a waveguide (32), which extends through handle assembly (20) to join transducer assembly (30) with blade (40). Thus, ultrasonic vibrations that are generated by transducer assembly (30) are communicated along waveguide (32) to blade (40), such that blade (40) will vibrate ultrasonically when transducer assembly (30) is activated. Those of ordinary skill in the art will understand that, as a matter of physics, the distal end of blade (40) is located at a position corresponding to an anti-node associated with resonant ultrasonic vibrations communicated through waveguide (32) (i.e., at an acoustic anti-node).

When transducer assembly (30) is energized, the distal end of blade (40) is configured to move longitudinally in the range of, for example, approximately 10 to 500 microns peak-to-peak, and in some instances in the range of about 20 to about 200 microns at a predetermined vibratory frequency $f_o$ of, for example, approximately 21 kHz to approximately 31 kHz. In some other versions, the vibratory frequency is up to approximately 50 kHz or even up to approximately 55 kHz. At any such frequencies, when blade (40) is pressed against bone as described in greater detail below, the ultrasonic oscillation of blade (40) will work in concert with sharp edge (42) to break up the bone to promote cutting of the bone by blade (40).

Liquid dispensing feature (50) of the present example is in the form of a tube having an open distal end that is located proximally of the proximal end of transverse opening (44). It should be understood that no portions of liquid dispensing feature (50) contact blade (40) in this example. Moreover, liquid dispensing feature (50) has sufficient rigidity in this example such that liquid dispensing feature (50) will not contact blade (40) even if liquid dispensing feature (50) is pressed against bone or other structures during normal operation of instrument (10).

The tube forming liquid dispensing feature (50) is parallel to waveguide (32) and blade (40) and is laterally offset from waveguide (32) and blade (40). Liquid dispensing feature (50) is in fluid communication with conduit (18) via port, such that liquid dispensing feature (50) is operable to expel cooling liquid from fluid source (16) via the open distal end of liquid dispensing feature (50). Due to the positioning of liquid dispensing feature (50) in relation to blade (40), the expelled cooling liquid will flow along blade (40) and along the bone that is being engaged by blade (40), thereby providing a cooling effect to blade (40) and the adjacent bone. As noted above, when an ultrasonic blade is used to cut through bone, the friction caused by the blade vibrating against the bone may generate substantial heat, which may be undesirable. Thus, liquid dispensing feature (50) may be used to dispense cooling liquid at a bone cut site in order to avoid undesirable effects from excess heat generated by blade (40).

In the present example, the distal end of liquid dispensing feature (50), including a distal-most end of liquid dispensing feature (50), is located at a position corresponding to a node associated with ultrasonic vibrations communicated along waveguide (32) and blade (40). This may reduce the occurrence of waveguide (32) or blade (40) undesirably dispersing cooling liquid laterally away from blade (40) as soon as the cooling liquid exits the distal end of liquid dispensing feature (50).

While liquid dispensing feature (50) is disclosed herein as having the form of a tube with an open distal end, it should be understood that liquid dispensing feature (50) may take a variety of other forms. By way of example only, liquid dispensing feature (50) may be configured and operable in accordance with any of the various liquid dispensing features described in U.S. patent application Ser. No. 15/163,811, entitled "Ultrasonic Surgical Instrument with Cooling Conduit," filed on May 25, 2016, published as U.S. Pub. No. 2017/0340344 on Nov. 30, 2017, the disclosure of which is incorporated by reference herein. Other suitable forms that liquid dispensing feature (50) may take will be apparent to those of ordinary skill in the art in view of the teachings herein.

Figure 2:
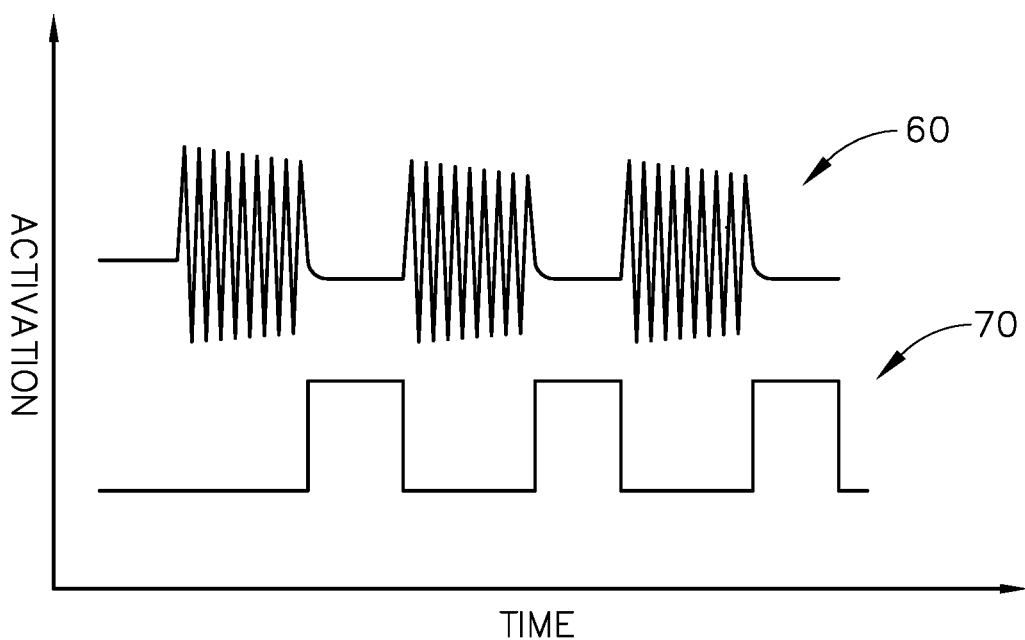
FIG. 2 depicts a graph showing an exemplary power profile that may be used to drive the instrument of FIG. 1, including an ultrasonic transducer driving signal and a fluid pump driving signal.
Figure 3:
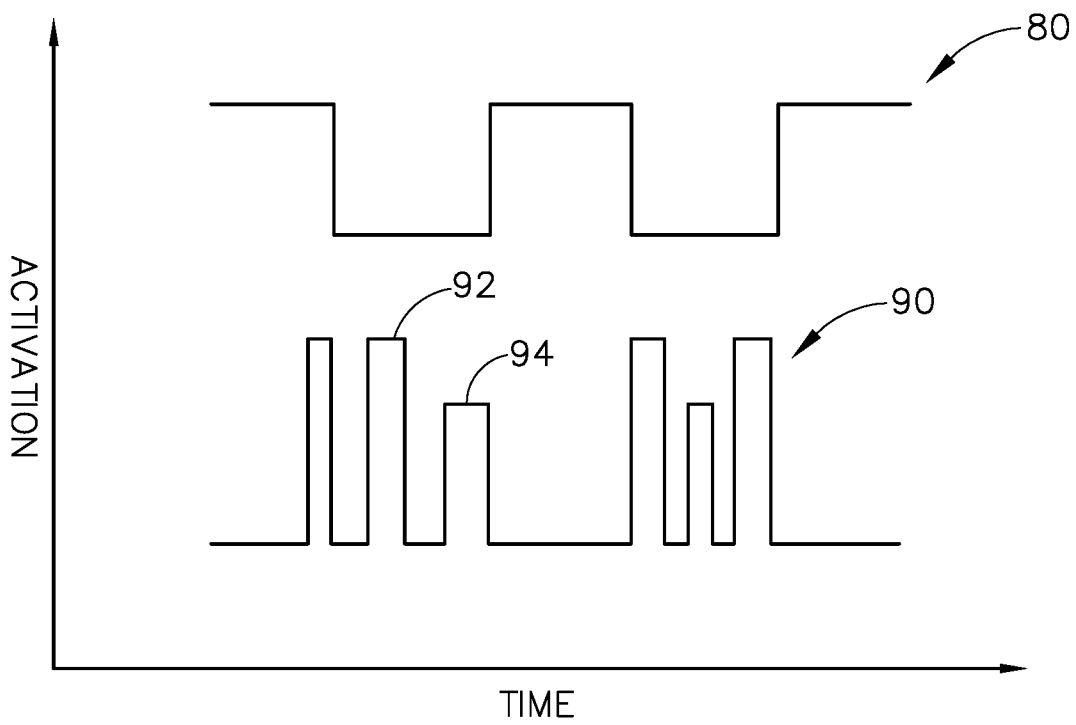
FIG. 3 depicts a graph showing another exemplary power profile that may be used to drive the instrument of FIG. 1, including an ultrasonic transducer driving signal and a fluid pump driving signal.

As noted above, generator (12) is operable to selectively activate the pump of fluid source (16). As also noted above, generator (12) is operable to selectively activate transducer assembly (30). FIGS. 2-3 show examples of ways in which generator (12) may alternate between activating the pump of fluid source (16) and generator (12). In particular, FIG. 2 shows a first plot (60) representing a control signal from generator (12) to drive transducer assembly (30); and a second plot (70) representing a control signal from generator (12) to drive the pump of fluid source (16). In this example, transducer assembly (30) is driven through pulses of electrical energy. In particular, transducer assembly (30) is driven using pulse width modulation (PWM).

Between each pulse of electrical energy to drive transducer assembly (30), the pump of fluid source (16) is driven through pulses of electrical energy. Thus, generator (12) alternates between driving transducer assembly (30) and the pump of fluid source (16). Driving transducer assembly (30) and the pump of fluid source (16) in such an alternating, pulsed fashion may reduce the occurrence of blade (40) converting the cooling liquid into a mist before the cooling liquid reaches the bone and the distal end of blade (40). In other words, driving transducer assembly (30) and the pump of fluid source (16) in an alternating, pulsed fashion may increase the amount of cooling liquid that reaches the bone and the distal end of blade (40). By way of example only, some versions may provide activation of transducer assembly (30) for approximately 90% of each minute of operation and activation of the pump of fluid source (16) for approximately the remaining 10% of each minute. Various suitable frequencies and durations that may be used for these alternating pulses will be apparent to those of ordinary skill in the art in view of the teachings herein.

In some versions, each pulse of electrical power that is used to drive the pump of fluid source (16) does not begin until the end of the most recent pulse of electrical power that is used to drive transducer assembly (30). In other words, the alternating pulses do not overlap at all in some examples. In some other examples, there is some overlap between the alternating pulses. For instance, each pulse of electrical power that is used to drive the pump of fluid source (16) may begin near the end of the most recent pulse of electrical power that is used to drive transducer assembly (30). As yet another merely illustrative example, each pulse of electrical power that is used to drive the pump of fluid source (16) may not begin until a certain resting duration has passed since the end of the most recent pulse of electrical power that is used to drive transducer assembly (30). As yet another merely illustrative example, pulsed electrical power may be used to drive transducer assembly (30), while the pump of fluid source (16) is driven constantly. This may provide alternating misting and flowing of the cooling liquid. Other suitable combinations and relationships between the different pulses will be apparent to those of ordinary skill in the art in view of the teachings herein. It should also be understood that the combinations and relationships between the different pulses may be selected and/or adjusted based on real-time feedback, including but not limited to the frequency slope feedback described in greater detail below.

FIG. 3 shows another exemplary set of plots (80, 90) representing a control signal from generator (12) to drive transducer assembly (30); and a control signal from generator (12) to drive the pump of fluid source (16). Plots (80, 90) are substantially identical to plots (60, 70) described above. Thus, in the example shows in FIG. 3, generator (12) alternates between driving transducer assembly (30) and the pump of fluid source (16). While plot (80) shows transducer assembly (30) being driven by a purely square wave power profile, it should be understood that transducer assembly (30) may be driven by some other kind of pulsing power profile (e.g., like the pulse width modulation represented by plot (60), etc.).

Unlike plot (70) described above, plot (90) provides a differently configured pattern of pulses (92, 94). In particular, the pump of fluid source (16) is driven by a combination of higher amplitude pulses (92) and lower amplitude pulses (94). The higher amplitude pulses (92) provide a stronger flow of cooling liquid from fluid source (16) than the flow provided by lower amplitude pulses (92). As shown, in a first fluid driving cycle, a first high amplitude pulse (92) overlaps with the power pulse provided to transducer assembly (30); while a second high amplitude pulse (92) and then a low amplitude pulse (94) are provided when transducer assembly (30) is between power pulses. In the second fluid driving cycle, a third high amplitude pulse (92) overlaps with the next power pulse provided to transducer assembly (30); while a low amplitude pulse (94) and then a fourth high amplitude pulse (92) are provided when transducer assembly (30) is between power pulses. Of course, this example is merely illustrative. The pump of fluid source (16) may be driven in any other suitable combination of high amplitude pulses (92) and low amplitude pulses (94). Moreover, high amplitude pulses (92) and low amplitude pulses (94) may have any other suitable relationship with the pulses that are used to drive transducer assembly (92). Various other suitable relationships and algorithms that may be used will be apparent to those of ordinary skill in the art in view of the teachings herein.

Other suitable ways in which a single generator (12) may be used to drive both an ultrasonic transducer assembly (30) and a pump of a fluid source (16) will be apparent to those of ordinary skill in the art in view of the teachings herein.

II. Exemplary Ultrasonic Surgical Instrument with Generator Controlled Liquid Cooling Valve In some instances, it may be desirable to provide an instrument (10) where fluid source (16) does not include a pump that is controlled by generator (12). For instance, some versions of instrument (10) may have a fluid source (16) that comprises a pump that is continuously activated. Some other versions of instrument (10) may have a passive fluid source that is simply a reservoir (e.g., a bag or other container) that provides fluid communication under the influence of gravity, without any kind of pumps. In these examples (and others lacking a pump that is controlled by generator (12)), it may nevertheless be desirable to have generator (12) still provide some degree of control over the flow of fluid from fluid source (16).

Figure 4:
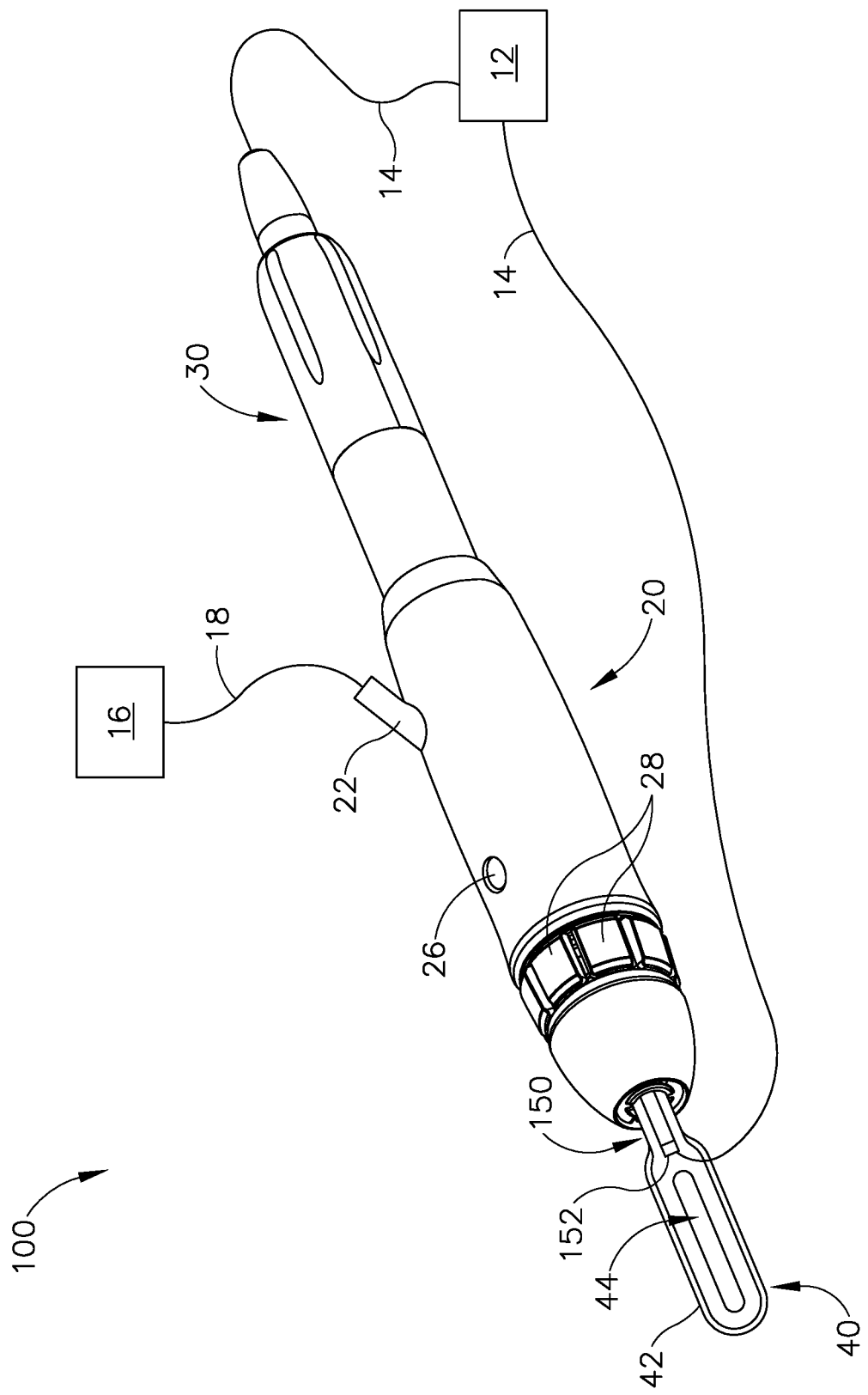
FIG. 4 depicts a perspective view of another exemplary ultrasonic surgical instrument.

FIG. 4 shows an exemplary ultrasonic surgical instrument (100) that lacks a pump that is controlled by generator (12). Instrument (100) of this example is substantially identical to instrument (10). In particular, instrument (100) of this example comprises a generator (12), a handle assembly (20), an ultrasonic transducer assembly (30), and an ultrasonic blade (40), all of which are identical to these same components (12, 20, 30, 40) of instrument (10) described above. The details of these components (and their sub-components) will therefore not be repeated here. Instrument (100) of this example also includes a fluid source (16). Fluid source (16) does not comprise a pump that is controlled by generator (12). In some versions, fluid source (16) of instrument comprises a pump that remains constantly activated. In some other versions, fluid source (16) consists of a reservoir (e.g., a bag or other container) that provides fluid communication under the influence of gravity, without any kind of pump. Other suitable forms that fluid source (16) may take will be apparent to those of ordinary skill in the art in view of the teachings herein.

Instrument (100) of this example differs from instrument (10) mainly due to the incorporation of a valve (152) in liquid dispensing feature (150). In the present example, the distal end of liquid dispensing feature (150) is located at a position corresponding to a node associated with ultrasonic vibrations communicated along waveguide (32) and blade (40). This may reduce the occurrence of waveguide (32) or blade (40) undesirably dispersing cooling liquid laterally away from blade (40) as soon as the cooling liquid exits the distal end of liquid dispensing feature (150).

Valve (152) is operable to selectively restrict or otherwise control the flow of cooling liquid from liquid dispensing feature (150) onto blade (40). In some versions, valve (152) comprises a simple on/off valve that switches between a fully open state and a fully closed state in a binary fashion. In some other versions, valve (152) comprises a proportional valve or variable orifice that is operable to transition among a range of various degrees of restriction. In other words, valve (152) may selectively adjust the flow of cooling liquid expelled from liquid dispensing feature (150) along a range of flow rates. Various suitable forms that valve (152) may take will be apparent to those of ordinary skill in the art in view of the teachings herein.

Valve (152) of the present example is controlled by generator (12). In some versions, generator (12) toggles valve (152) between a fully opened state and a fully closed state. It should be understood that, in such versions, valve (152) may be driven with an activation profile similar to that shown as plot (70) in FIG. 2. In other words, valve (152) may be fully closed when transducer assembly (30) is being activated; and valve (152) may be fully opened when transducer assembly (30) is not being activated. Alternatively, valve (152) may be selectively opened or closed in any other suitable relationship (or in no relationship at all) relative to activation of activation of transducer assembly (30).

In versions where valve (152) comprises a proportional valve or variable orifice, etc., generator (12) may selectively vary the liquid flow rate based on various factors. For instance, generator (12) may selectively vary the liquid flow rate through valve (152) based on a predetermined fluid communication profile. Alternatively, generator (12) may selectively vary the liquid flow rate through valve (152) based on real time feedback, such as temperature related feedback, acoustic feedback as described in greater detail below, and/or based on any other kind of feedback. In some versions, the delivery of liquid is regulated based on indirect measurement of the temperature of blade (40), such as by monitoring frequency shift or slope. A merely illustrative example of this is described below with reference to FIG. 6.

Other suitable ways in which generator (12) may selectively activate valve (152) or otherwise drive valve (152) will be apparent to those of ordinary skill in the art in view of the teachings herein.

III. Exemplary Ultrasonic Surgical Instrument with Transducer Actuated Liquid Cooling Reservoir In some instances, it may be desirable to incorporate a fluid source directly into an ultrasonic surgical instrument. This may prevent the ultrasonic surgical instrument from having to be coupled to a separate fluid source via a tube or other fluid conduit. It should be understood that instruments (10, 100) described above may be configured such that their fluid sources (16) are integrated directly into the body of instrument (10, 100) (e.g., encased in handle assembly (20)).

Figure 5:
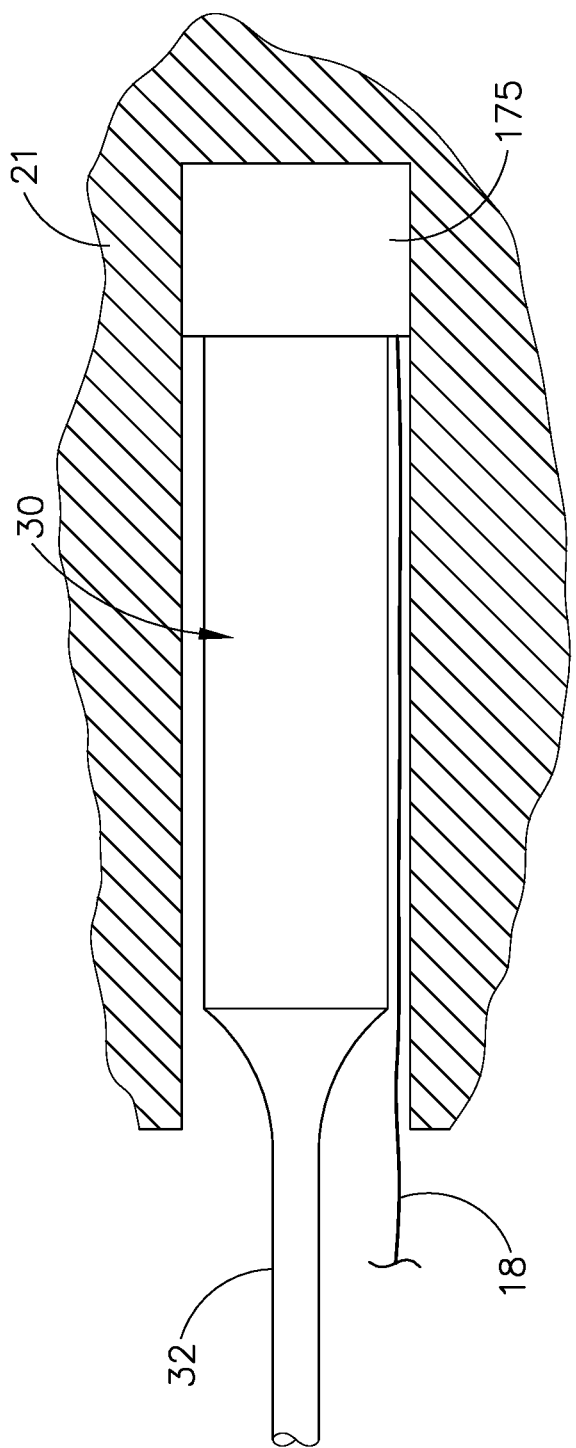
FIG. 5 depicts a partial cross-sectional view of an exemplary ultrasonically driven fluid source that may be incorporated into the instrument of FIG. 1 or the instrument of FIG. 4.

It may also be desirable to provide an integrated fluid source that is activated directly by transducer assembly (30), such that the integral fluid source dispenses a cooling liquid each time transducer assembly (30) is activated. To that end, FIG. 5 shows an exemplary fluid source (175) that is integrated into an ultrasonic surgical instrument such as instrument (10, 100). In particular, fluid source (175) of this example is positioned between transducer assembly (30) and a housing (21) of handle assembly (20).

Fluid source (175) has a deformable body in this example. Housing (21) is configured to provide a mechanical ground, such that transducer assembly (30) urges fluid source (175) against housing (21) in a vibrating fashion when transducer assembly (30) is activated. When fluid source (175) is vibrationally driven against housing (21) by transducer assembly (30), fluid source (175) deforms such that fluid source (175) expels cooling liquid via conduit (18). As described above with respect to instruments (10, 100), conduit (18) is coupled with a liquid dispensing feature (50, 150), such that cooling liquid expelled from fluid source (175) will cool blade (40) and the bone adjacent to blade (40). In some versions, fluid source (175) comprises a pressurized cooling liquid such that fluid source (175) has increased sensitivity to vibrational movement from transducer assembly (30). Various suitable forms that fluid source (175) may take, and various suitable ways in which transducer assembly (30) may actuate fluid source (175) to drive cooling liquid from fluid source when transducer assembly (30) is activated, will be apparent to those of ordinary skill in the art in view of the teachings herein.

IV. Exemplary Ultrasonic Surgical Instrument with Liquid Cooling Based on Acoustic Feedback As noted above, generator (12) may provide coordinated control of the activation of transducer assembly (30) and the flow of cooling liquid onto blade (40) and the bone adjacent to blade (40). In instrument (10), generator (12) controls the flow of cooling liquid by selectively activating a pump in fluid source (16). In instrument (100), generator (12) controls the flow of cooling liquid by selectively activating valve (152) of liquid dispensing feature (150). In either case, and in other examples where an instrument is capable of providing some form of control over the activation of transducer assembly (30) and the flow of cooling liquid onto blade (40) and the bone adjacent to blade (40), the control algorithm may be based on real time feedback. While the present example is provided in the context of a single generator (12) providing control of the activation of transducer assembly (30) and the flow of cooling liquid, it should be understood that the teachings herein may also be applied to versions where different components provide control of the activation of transducer assembly (30) and the flow of cooling liquid.

Figure 6:
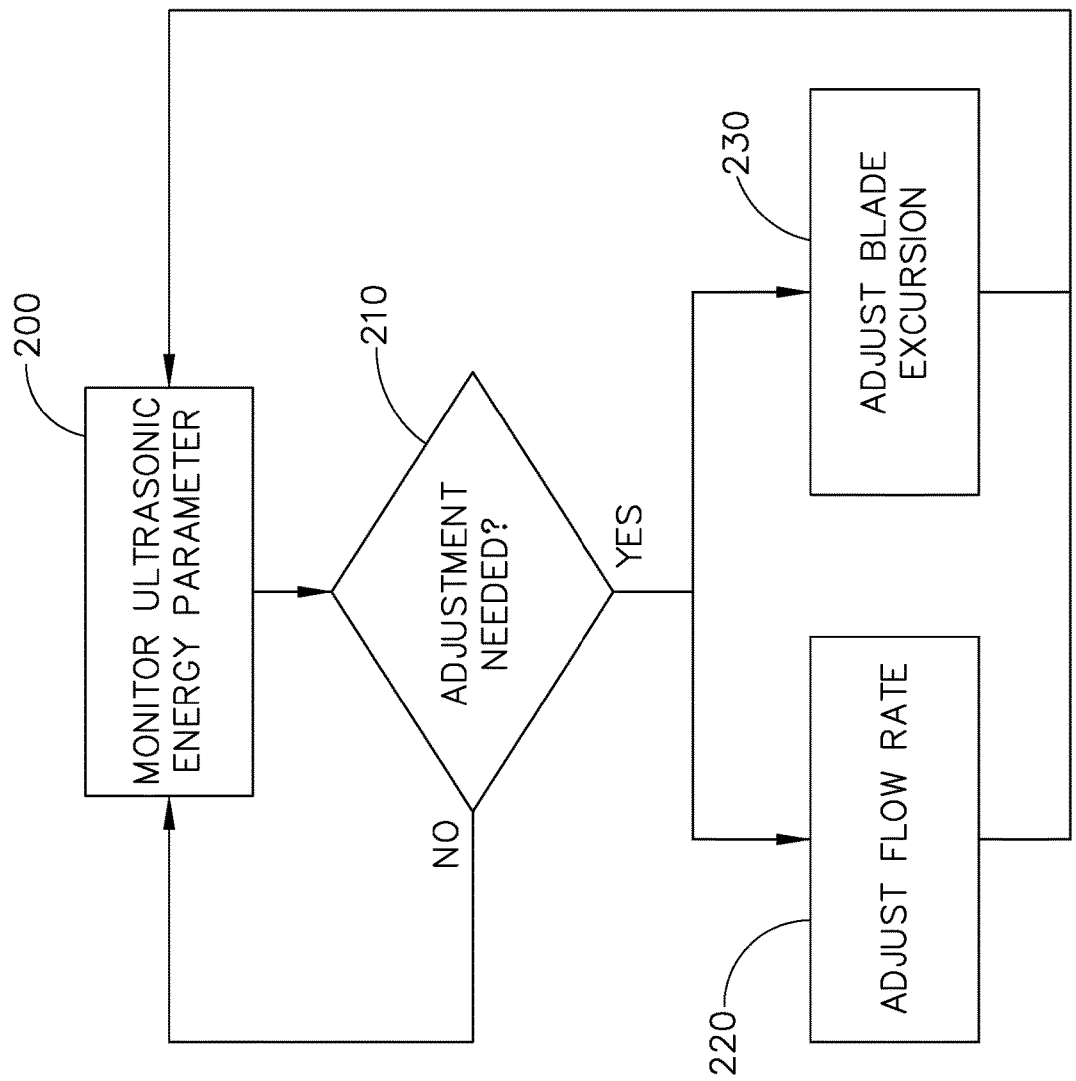
FIG. 6 depicts a flow chart showing an exemplary method of operating the instrument of FIG. 1 or the instrument of FIG. 4.
Figure 7:
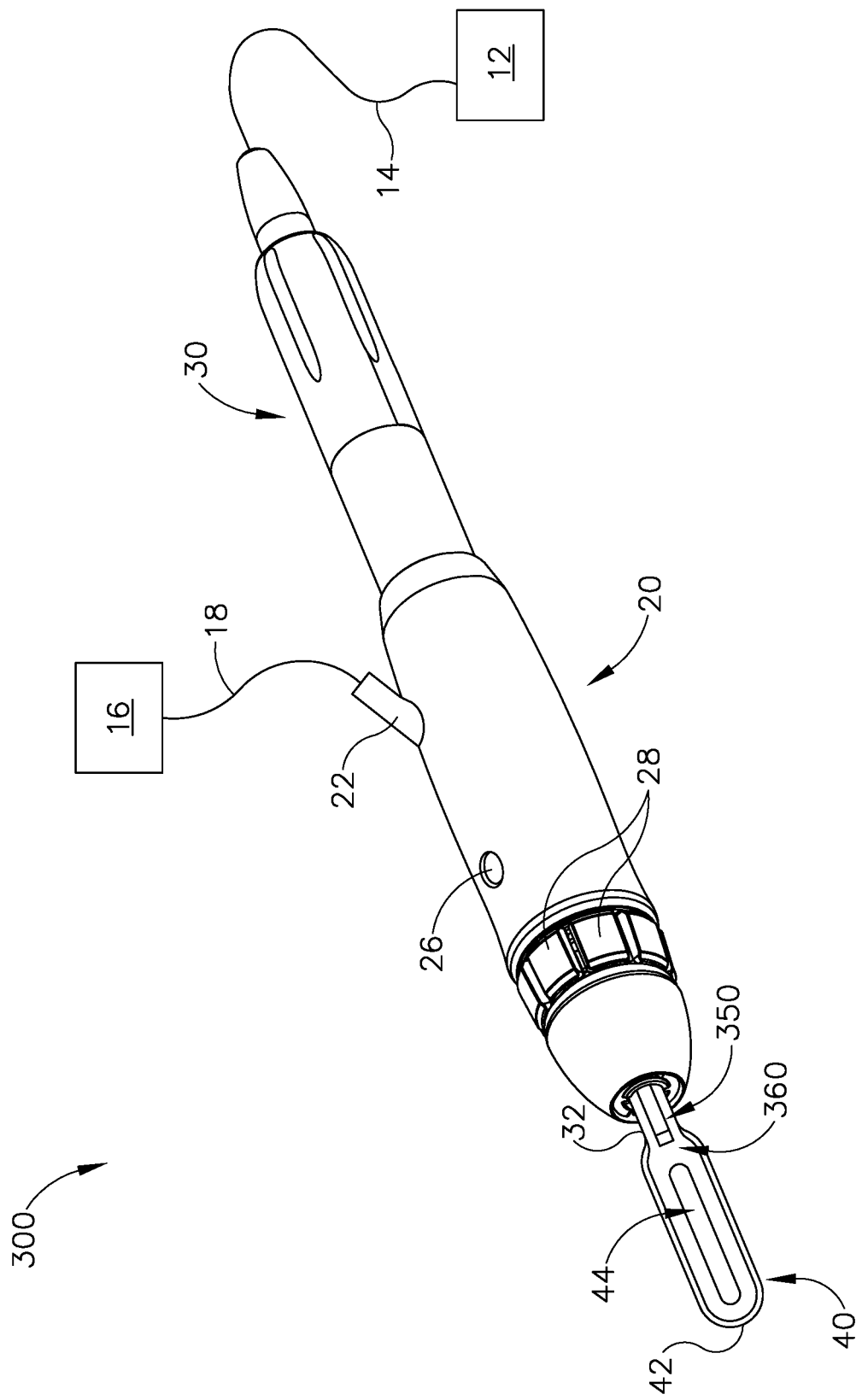
FIG. 7 depicts a perspective view of yet another exemplary ultrasonic surgical instrument.

FIG. 6 shows an exemplary method whereby an ultrasonic surgical instrument (10, 100) adjusts the activation of transducer assembly (30) and the flow of cooling liquid based on real time feedback. In particular, block (200) shows how instrument (10, 100) monitors one or more ultrasonic energy parameters during use of instrument (10, 100) in a surgical procedure. By way of example only, this monitoring may include monitoring acoustic feedback via blade (40), waveguide (32), transducer assembly (30), generator (12), and/or user inputs. Various suitable ways in which acoustic feedback may be monitored via blade (40), waveguide (32), transducer assembly (30), generator (12), and/or user inputs will be apparent to those of ordinary skill in the art in view of the teachings herein. As another merely illustrative example, the monitoring of block (200) may include using known techniques to monitor the frequency slope of the control signal driving transducer assembly (30) and/or monitoring the electrical impedance of transducer assembly (30). In some instances, blade (40) may become slightly elongated when blade (40) becomes heated, and this elongation of blade (40) may cause a drop in the resonant frequency (e.g., as much as a 1 kHz drop in frequency). Thus, the frequency slope may provide an indication of the temperature of blade (40), since the frequency may decrease as the temperature increases. It should be understood that generator (12) may be capable of monitoring frequency slope and/or electrical impedance.

In addition to or as an alternative to frequency slope and/or electrical impedance as a basis to adjust the activation of transducer assembly (30) and/or the flow of cooling liquid, instrument (10, 100) may monitor power consumption of transducer assembly (30), time of activation of transducer assembly (30), and other filtered and time derivatives of the frequency, impedance or power consumption (e.g., the average frequency change across the previous 10, 50 or 100 samples). Moreover, the conditions of the cooling liquid itself may be monitored as a basis to adjust the activation of transducer assembly (30) and/or the flow of cooling liquid. For instance, a control algorithm may factor in the rate of cooling liquid delivery combined with the rate of cooling to determine whether an adjustment is warranted. As another merely illustrative example, a low cooling liquid condition could lead to adjustments in cooling liquid outputs. Other kinds of conditions that may monitored (e.g., conditions of blade (40), conditions of the bone adjacent to blade (40), and/or other conditions), and various ways in which such other kinds of conditions may monitored, will be apparent to those of ordinary skill in the art in view of the teachings herein.

It should also be understood that more than one ultrasonic energy parameter may be monitored during performance of block (200). Moreover, instrument (10, 100) may monitor other conditions in addition to or as an alternative to monitoring one or more ultrasonic energy parameters. By way of example only, instrument (10, 100) may monitor the temperature of blade (40), frequency slope, and/or other conditions that may be indicative of the need to make adjustments (blocks 220, 230) as described below.

Block (210) shows how the real-time feedback is evaluated to determine whether an adjustment is needed. By way of example only, this evaluation may be performed by executing a control logic in generator (12). Alternatively, this evaluation (block 210) may be performed by executing a control logic in handle assembly (20) and/or elsewhere in instrument (10, 100). This evaluation (block 210) may include comparing one or more sensed values against a predetermined threshold value, to determine whether the value exceeds or falls below the threshold value. In addition or in the alternative, this evaluation (block 210) may include determining whether a certain combination of conditions is present, by comparing sensed conditions to a predetermined set of condition criteria. Other suitable forms that the evaluation (block 210) may take will be apparent to those of ordinary skill in the art in view of the teachings herein.

If the evaluation (block 210) determines that an adjustment is not needed, then the ultrasonic energy parameter continues to be monitored (block 200) and no adjustments are made. However, if the evaluation (block 210) determines that an adjustment is needed, then the flow rate of the cooling liquid is adjusted (block 220) and/or the blade (40) excursion (i.e., the amplitude of the motion of blade (40)) is adjusted (block 230). It should be understood that the goal of adjustments (blocks 220, 230) may be to provide optimized cooling to blade (40) and the bone at the surgical site, without unnecessarily flooding the surgical site with excessive cooling liquid.

Adjustment of the cooling liquid (block 220) may include either increasing the flow of cooling liquid or reducing the flow of cooling liquid. As noted above, the flow may be adjusted by adjusting the control of a pump that drives a cooling liquid and/or by adjusting the state of a valve that regulates flow of cooling liquid. It should also be understood that adjustment of the cooling liquid (block 220) may include changing a pulse pattern associated with the flow of cooling liquid. Other suitable ways in which communication of cooling liquid may be adjusted (block 220) will be apparent to those of ordinary skill in the art in view of the teachings herein.

Adjustment of blade (40) excursion (block 230) may include adjusting the mechanical displacement of blade (40) by varying the power signal that is sent to transducer assembly (30). In addition or in the alternative, adjustment of blade (40) excursion (block 230) may include phasing or pulsing the amplitude of blade (40) between higher and lower amplitude. In some such versions, the flow rate of the cooling liquid may be increased in accordance with the higher amplitude excursion of blade (40); while the flow rate of the cooling liquid may be decreased in accordance with the lower amplitude excursion of blade (40). Alternatively, the changes in flow cooling liquid rate may be provided out of phase with the changes in blade (40) excursion. In other words, the flow rate of the cooling liquid may be decreased in accordance with the higher amplitude excursion of blade (40); while the flow rate of the cooling liquid may be increased in accordance with the lower amplitude excursion of blade (40). Other suitable ways in which excursion of blade (40) may be adjusted (block 220) will be apparent to those of ordinary skill in the art in view of the teachings herein.

In some instances, the flow rate of the cooling liquid is adjusted (block 220) and the blade (40) excursion is adjusted (block 230) simultaneously or in a sequence. In some other instances, the flow rate of the cooling liquid is adjusted (block 220) without the blade (40) excursion being adjusted (block 230). In still other versions, the blade (40) excursion is adjusted (block 230) without the flow rate of the cooling liquid being adjusted (block 220). Various suitable combinations, sequences, and permutations of adjustments (blocks 220, 230) will be apparent to those of ordinary skill in the art in view of the teachings herein.

In some versions, a control logic residing in generator (12) performs the act of adjusting the flow rate of the cooling liquid (block 220) and also the act of adjusting the blade (40) excursion (block 230). In some other versions, a control logic residing in handle assembly (20) and/or elsewhere in instrument (10, 100) performs the act of adjusting the flow rate of the cooling liquid (block 220) and also the act of adjusting the blade (40) excursion (block 230). In still other versions, a control logic residing in handle assembly (20) and/or elsewhere in instrument (10, 100) performs the act of adjusting the flow rate of the cooling liquid (block 220); while a control logic residing in generator (12) performs the act of adjusting the blade (40) excursion (block 230). Still other suitable ways in which the adjustments (blocks 220, 230) may be executed will be apparent to those of ordinary skill in the art in view of the teachings herein.

After one or both adjustments (blocks 220, 230) is/are made, the ultrasonic energy parameter(s) is/are again monitored (block 200) to determine whether further adjustments are warranted (block 210). Thus, ultrasonic instrument (10, 100) may continue to operate in a real time feedback loop, making ad hoc adjustments as needed based on conditions that are sensed in real time. This may provide best tailored application of cooling liquid to blade (40) and adjacent bone, maximizing the cooling effect while minimizing the application of excessive cooling liquid.

V. Exemplary Ultrasonic Surgical Instrument with Thermally Actuated Liquid Cooling Valve While the method described above with respect to FIG. 6 provides adjustment of the flow of cooling liquid based on sensed conditions, the above described method requires some processing of data. It may be desirable to provide real time adjustment of the flow of cooling liquid based on a real time condition without requiring the processing of data. To that end, FIGS. 7-9B show an exemplary instrument (300) that provides an adjusted flow of cooling liquid based on the temperature of blade (40).

Instrument (300) of the present example of this example is substantially identical to instrument (10). In particular, instrument (300) of this example comprises a generator (12), a fluid source (16), a handle assembly (20), an ultrasonic transducer assembly (30), and an ultrasonic blade (40), all of which are identical to these same components (12, 16, 20, 30, 40) of instrument (10) described above. The details of these components (and their sub-components) will therefore not be repeated here. Instrument (300) of this example differs from instrument (10) in that instrument (300) includes a liquid dispensing feature (350) having a temperature sensitive valve (360). In the present example, the distal end of liquid dispensing feature (350) is located at a position corresponding to a node associated with ultrasonic vibrations communicated along waveguide (32) and blade (40). This may reduce the occurrence of waveguide (32) or blade (40) undesirably dispersing cooling liquid laterally away from blade (40) as soon as the cooling liquid exits the distal end of liquid dispensing feature (350).

Figure 8:
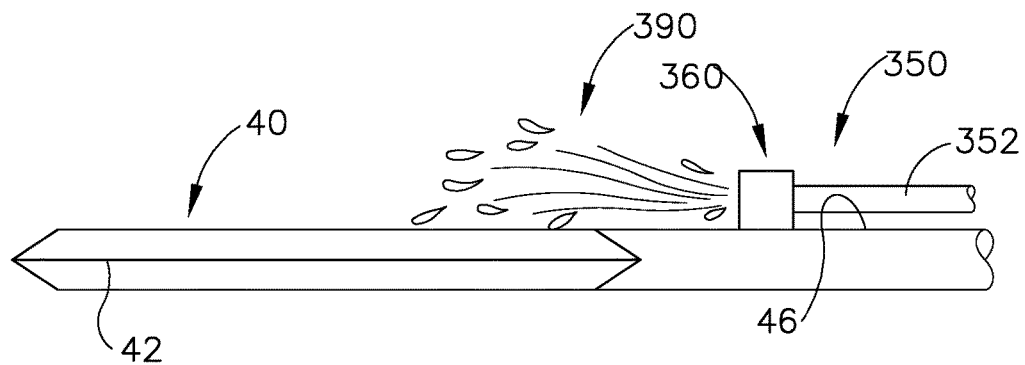
FIG. 8 depicts a side elevational view of the blade and valve assembly of the instrument of FIG. 7.
Figures 9A, 9B:
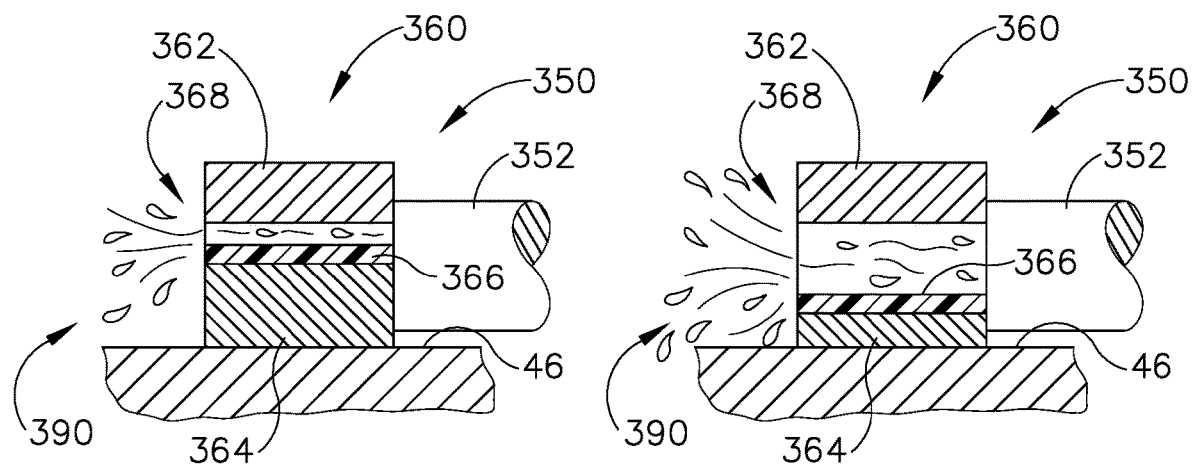
FIG. 9A depicts a cross-sectional side view of the valve assembly of FIG. 8, with the valve assembly in a first state.
FIG. 9B depicts a cross-sectional side view of the valve assembly of FIG. 8, with the valve assembly in a second state.

As best seen in FIGS. 8-9B, temperature sensitive valve (360) is mounted directly to a surface (46) of blade (40). The distal end of a fluid conduit (352) is coupled with temperature sensitive valve (360). The proximal end of fluid conduit (352) is in fluid communication with port (22), such that fluid conduit (352) receives a cooling liquid from fluid source (16) via conduit (18) and port (22).

As shown in FIGS. 9A-9B, valve (360) comprises an upper grounding portion (362), a temperature sensitive lower portion (364), and an insulating portion (366). Upper grounding portion (362) is configured to maintain a fixed position and configuration relative to surface (46) of blade (40), such that upper grounding portion (362) provides a mechanically grounding structure.

Temperature sensitive lower portion (364) is formed of a temperature sensitive material, such that temperature sensitive lower portion (364) contracts in response to relatively high temperatures; and such that temperature sensitive lower portion (364) expands in response to relatively low temperatures. In particular, FIG. 9A shows temperature sensitive lower portion (364) in an expanded state, where blade (40) is at a relatively low temperature. FIG. 9B shows temperature sensitive lower portion (364) in a contracted state, where blade (40) is at a relatively high temperature. By way of example only, temperature sensitive lower portion (364) may comprise bimetal, thermally expanding wax, and/or any other suitable material(s).

Insulating portion (366) is mounted directly to temperature sensitive lower portion (364). Insulating portion (366) is configured to provide thermal isolation between temperature sensitive lower portion (364) and the cooling liquid (390) that is expelled through valve (360). Thus, when blade (40) becomes substantially hot during normal operation of instrument (300) in a surgical procedure, insulating portion (366) prevents the heat of blade (40) from prematurely vaporizing cooling liquid (390). Insulating portion (366) also cooperates with upper grounding portion (362) to define a variable orifice (368), through which cooling liquid (390) is communicated.

Since insulating portion (366) is mounted directly to temperature sensitive lower portion (364), since temperature sensitive lower portion (364) expands and contracts based on the temperature of blade (40), and since upper grounding portion (362) maintains a fixed position and configuration, the size of variable orifice (368) will change based on the temperature of blade (40). In particular, when blade (40) is relatively cool, variable orifice (368) is relatively small as shown in FIG. 9A. This provides a reduced flow of cooling liquid (390) through valve (360). This may prevent the surgical site from being unnecessarily flooded with cooling liquid (390), which some operators may find undesirable due to adverse effects on visibility, etc.

When blade (40) is relatively hot, variable orifice (368) is relatively large as shown in FIG. 9B. This provides an increased flow of cooling liquid (390) through valve (360). It should therefore be understood that, the hotter blade (40) becomes, the more cooling liquid (390) flows through valve (360). By way of example only, valve (360) may be configured to keep blade (40) at or below a temperature of approximately 100° C. Alternatively, any other suitable target temperature may be used. It should be understood that the selection of materials used to form temperature sensitive lower portion (364), the amount of material used to form temperature sensitive lower portion (364), and/or other aspects of valve (360) may be varied to "tune in" the target temperature.

While FIGS. 9A-9B show valve (360) transitioning between a first open state and a second open state, in some versions valve (360) may be capable of achieving a fully closed state (e.g., when blade (40) is within a range between room temperature and some slightly higher temperature). Thus, in such versions no cooling liquid (390) will pass through valve (360) when the temperature is below a certain threshold. It should also be understood that valve (360) may be capable of providing various orifice sizes between and beyond those shown in FIGS. 9A-9B. It should also be understood that some versions of instrument (300) may have two or more valves (360). In such versions, valves (360) may be located at different positions relative to blade (40), thereby providing greater localization to the cooling effects from cooling liquid (390).

VI. Exemplary Ultrasonic Surgical Instrument with Liquid Cooling and Reciprocating Ultrasonic Blade In some instances where an ultrasonic blade (40) is disposed in bone, it may be difficult for a cooling liquid to reach the distal end of ultrasonic blade (40). In addition or in the alternative, the structure of blade (40) may be occupying the cut formed in the bone to the point where the cooling liquid cannot enter the cut formed in the bone. In addition or in the alternative, fine bone particles may fill part of the cut formed in the bone, making it difficult for cooling liquid to reach the bone cut surface. Thus, the cooling liquid may be incapable of providing a desired cooling effect to the distal end of ultrasonic blade (40) and the bone that is adjacent to the distal end of ultrasonic blade (40). In some instances, transverse opening (44) in blade (40) may promote the communication of cooling liquid to the distal end of ultrasonic blade (40) and the bone that is adjacent to the distal end of ultrasonic blade (40). However, there may be instances where a blade (40) lacks transverse opening (44) or instances where transverse opening (44) is fully disposed in the bone such that transverse opening (44) does not provide a path of communication of cooling liquid to the distal end of ultrasonic blade (40). It may therefore be desirable to provide an additional movement of blade (40) relative to the bone to promote access of the cooling liquid to the distal end of ultrasonic blade (40) and the bone that is adjacent to the distal end of ultrasonic blade (40).

Figure 10:
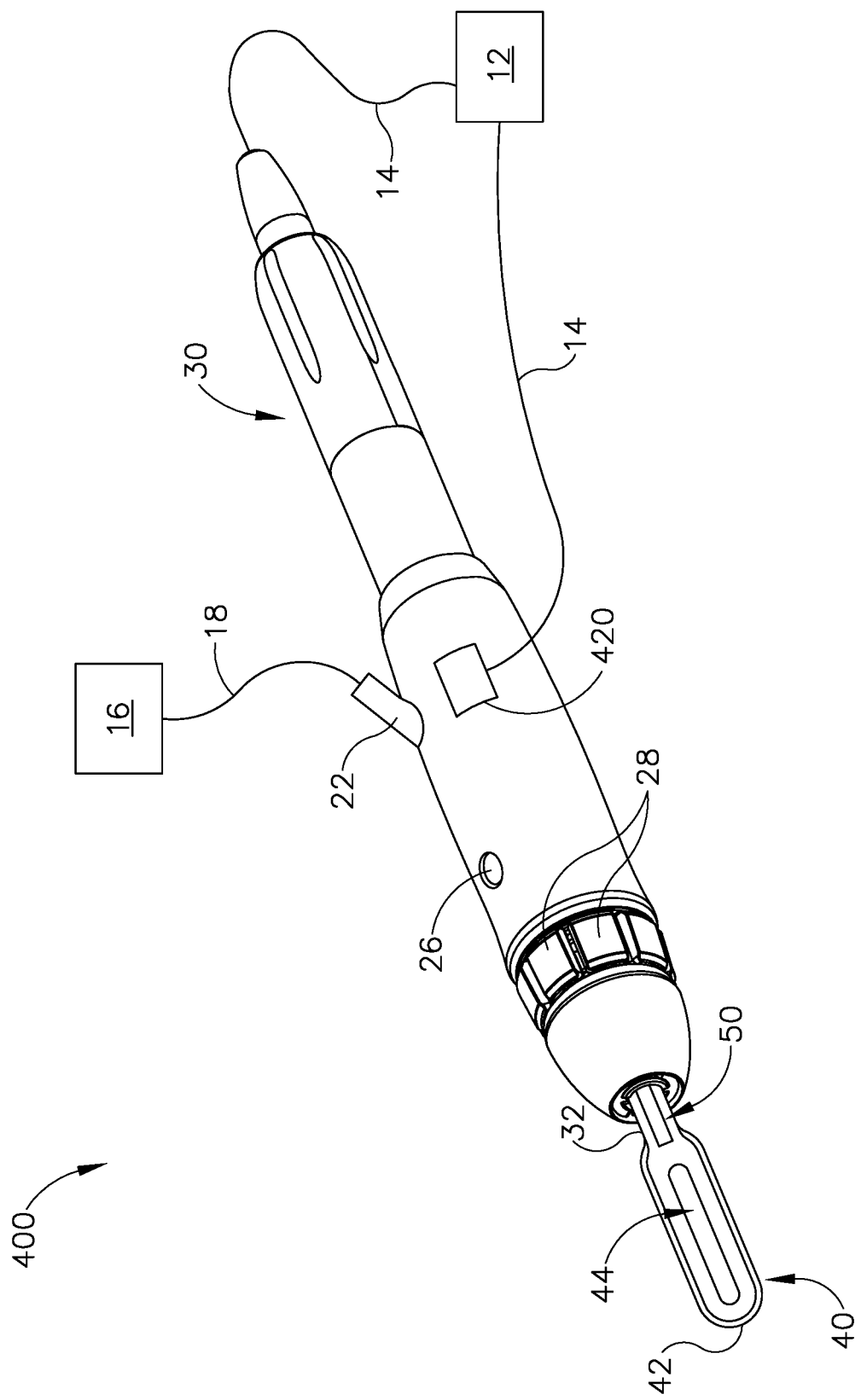
FIG. 10 depicts a perspective view of yet another exemplary ultrasonic surgical instrument.
Figure 11A:
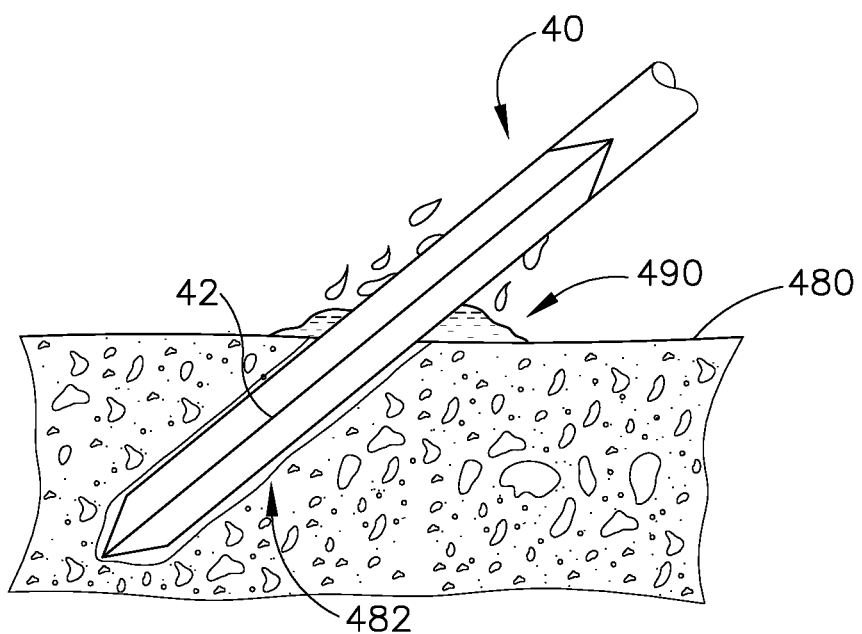
FIG. 11A depicts a side elevational view of an ultrasonic blade of the instrument of FIG. 10 disposed in bone, with the blade in a first state.
Figure 11B:
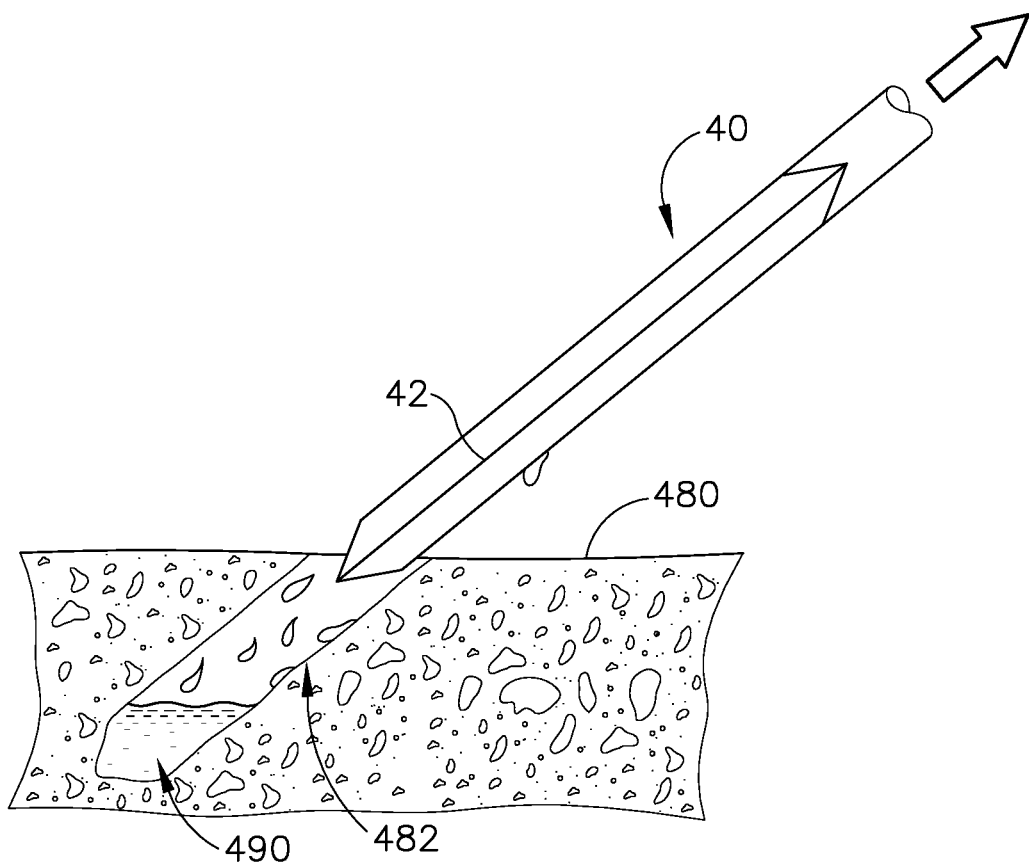
FIG. 11B depicts a side elevational view of an ultrasonic blade of the instrument of FIG. 10 disposed in bone, with the blade in a second state.
Figure 12:
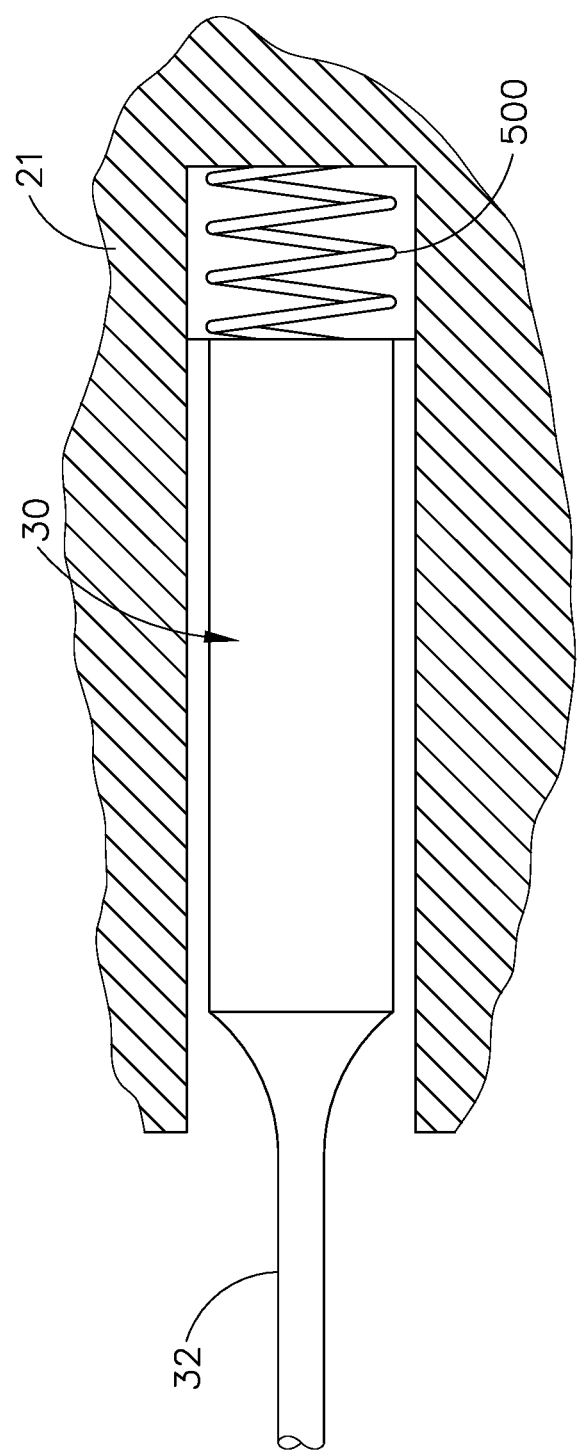
FIG. 12 depicts a partial cross-sectional view of an exemplary resiliently biased ultrasonic transducer assembly.

FIGS. 10-12 show an exemplary alternative instrument (400) that is operable to provide two different kinds of movement to blade (40)—an ultrasonic vibrational movement and a gross reciprocation movement. For purposes of this disclosure, the term "gross reciprocation" is meant to include longitudinal reciprocating movement having a higher amplitude and lower frequency than the ultrasonic vibrational movement. In the present example, the frequency of movement during gross reciprocation is too low to be considered an ultrasonic frequency. By way of example only, the amplitude of the gross reciprocation may be between approximately 0.040 inches and approximately 0.050 inches. Instrument (400) of the present example of this example is substantially identical to instrument (10). In particular, instrument (400) of this example comprises a generator (12), a fluid source (16), a handle assembly (20), an ultrasonic transducer assembly (30), an ultrasonic blade (40), and a liquid dispensing feature (50), all of which are identical to these same components (12, 16, 20, 30, 40, 50) of instrument (10) described above. The details of these components (and their sub-components) will therefore not be repeated here.

Instrument (400) of this example differs from instrument (10) in that instrument (300) includes a blade reciprocating feature (420) that is operable to provide the gross reciprocation movement to blade (40). In the present example, blade reciprocating feature (420) is in communication with generator (12) via a cable (14), such that generator (12) is configured to provide the electrical power and/or control signals to activate blade reciprocating feature (420). In some other versions, some other component (e.g., a component located in handle assembly (20)) is configured to provide the electrical power and/or control signals to activate blade reciprocating feature (420). By way of example only, blade reciprocating feature (420) may comprise a solenoid or a linear motor. As another merely illustrative example, blade reciprocating feature (420) may comprise a rotary motor coupled with a rack and pinion assembly. Other suitable forms that blade reciprocating feature (420) may take will be apparent to those of ordinary skill in the art in view of the teachings herein.

FIGS. 11A-11B show one merely illustrative example of how the gross reciprocation movement of blade (40) may promote communication of cooling liquid (490). In particular, FIG. 11A shows blade (40) in a distal position where blade (40) is fully disposed in a kerf (482) that is formed in bone (480) by blade (40). In this state, cooling liquid (490) that is dispensed from liquid dispensing feature (490) simply pools up outside of the kerf (482). Thus, the cooling liquid (490) does not reach the distal end of blade (40) or the walls of kerf (482). The cooling liquid (490) therefore does not provide optimized cooling of blade (40) or the bone (480) adjacent to blade (40). However, when blade (40) is grossly translated proximally to the position shown in FIG. 11B, the repositioning of blade (40) relative to bone (480) enables the cooling liquid (490) to travel along the full length of blade (40), such that the cooling liquid (490) is able to reach the distal end of blade (40). Moreover, the repositioning of blade (40) relative to bone (480) enables the cooling liquid (490) to travel into the kerf (482), such that the cooling liquid (490) is able to traverse the full length of kerf (482).

In some versions, blade (40) maintains the position shown in FIG. 11B for a certain predetermined duration (e.g., approximately 100 ms), then transitions back to the position shown in FIG. 11A. After reaching the state shown in FIG. 11B, blade (40) may rapidly transition back to the position shown in FIG. 11A; and reciprocate between the positions shown in FIGS. 11A and 11B one or more times. During this reciprocation, blade (40) may continue to vibrate ultrasonically to further cut bone (480). Alternatively, blade (40) may alternate between gross reciprocation and ultrasonic vibration in any number of permutations. By way of further example only, blade (40) may continuously vibrate ultrasonically; and provide one, two, or any other suitable number of reciprocations between the positions shown in FIGS. 11A and 11B on some periodic basis (e.g., every three seconds). Other suitable combinations of ultrasonic movement and gross reciprocation movement will be apparent to those of ordinary skill in the art in view of the teachings herein.

While FIG. 11B shows blade (40) substantially exiting the kerf (482) to enable cooling liquid (490) to enter the kerf (482), it should be understood that this range of gross motion may not be necessary in order to adequately enable cooling liquid (490) to enter the kerf (482). For instance, the presence of transverse opening (44) may enable cooling liquid (490) to adequately reach the kerf (482) without requiring blade (40) to substantially exit the kerf (482) during the gross reciprocating movement. It should also be understood that the operator may simply hold their hand steady relative to bone (480) during the gross reciprocation shown in FIGS. 11A-11B. In other words, the operator does not need to manually provide the gross reciprocation shown in FIGS. 11A-11B by advancing and retracting their hand (that is gripping handle assembly (20)) toward and away from bone (480). Since blade (40) is coupled with waveguide (32) and transducer assembly (30) as a unitary structure in the present example, it should be understood that waveguide (32) and transducer assembly (30) will also move longitudinally relative to handle assembly (20) and bone (480) while blade (40) moves longitudinally relative to handle assembly (20) and bone (480) during gross reciprocation.

In the example provided above, the gross translation of blade (40) is provided actively by sending electrical power to a dedicated blade reciprocating feature (420). FIG. 12 shows an exemplary alternative form of passive gross reciprocation features. In particular, FIG. 12 shows an example where transducer assembly (30) is coupled with a resilient member (500). Resilient member (500) is mechanically grounded against a housing (21) of handle assembly (20). In the present example, resilient member (500) comprises a coil spring. In some other versions, resilient member (500) comprises one or more leaf springs. Other suitable forms that resilient member (500) may take will be apparent to those of ordinary skill in the art in view of the teachings herein.

Resilient member (500) is configured to provide resonance at a frequency that is lower than the ultrasonic frequency at which blade (40) vibrates to cut bone (480). In particular, when transducer assembly (30) is activated to generate ultrasonic vibrations, transducer assembly (30) may mechanically react against resilient member (500). When this occurs, resilient member (500) may resonate at a relatively low frequency (i.e., lower than an ultrasonic frequency). This low frequency resonance may cause transducer assembly (30), waveguide (32), and blade (40) to reciprocate longitudinally at the relatively low frequency. This low frequency reciprocation of blade (40) may be considered gross reciprocation; and may provide the kind of movement depicted in FIGS. 11A-11B and described above. Various suitable ways in which resilient member (500) may be configured and tuned to provide an appropriate low frequency resonance will be apparent to those of ordinary skill in the art in view of the teachings herein.

While gross reciprocation is described herein in the context of a separate instrument (400), it should be understood that the foregoing teachings associated with gross reciprocation may be readily incorporated into any of the other instruments (100, 200, 300) described herein. In other words, gross reciprocation may be provided in combination with any of the other functionalities described above in the context of instruments (100, 200, 300).

It should also be understood that blade (40) may be activated to provide other kinds of movement (i.e., movement that would not necessarily constitute gross reciprocation) that may provide the above-described results provided by gross reciprocation. For instance, in addition to or in lieu of providing gross reciprocation of blade (40), the ultrasonic vibration of blade (40) may be modulated to provide transverse, non-axial vibrations that widen the kerf, thereby providing a kerf that is substantially wider than the width/thickness of blade (40). This additional width may provide clearance for cooling liquid to flow into the kerf and along the distal portion of blade (40), without necessarily having to provide gross reciprocation of blade (40). By way of example only, the ultrasonic vibration of blade (40) may be modulated to provide transverse, non-axial vibrations by pulsing a slightly different frequency, which may force a torsional twist of blade (40). Such movement of blade (40) may effectively cut outwardly from the central longitudinal axis of blade (40). Other suitable ways in which the ultrasonic vibration of blade (40) may be modulated to provide transverse, non-axial cutting motion will be apparent to those of ordinary skill in the art in view of the teachings herein.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body assembly; (b) an acoustic waveguide; (c) an ultrasonic blade positioned distally relative to the body assembly, wherein the ultrasonic blade is in acoustic communication with the acoustic waveguide; (d) a liquid dispensing feature positioned distally relative to the body assembly, wherein the liquid dispensing feature is positioned adjacent to the ultrasonic blade, wherein the liquid dispensing feature is configured to deliver a flow of cooling liquid to the ultrasonic blade; and (e) a control module, wherein the control module is operable to regulate fluid flow through the liquid dispensing feature

Example 2

The apparatus of Example 1, further comprising an ultrasonic transducer assembly coupled with the acoustic waveguide, wherein the control module is further operable to activate the ultrasonic transducer assembly.

Example 3

The apparatus of any one or more of Examples 1 through 2, further comprising a pump in fluid communication with the liquid dispensing feature.

Example 4

The apparatus of Example 3, wherein the control module is operable to selectively activate the pump to thereby regulate flow of cooling liquid through the liquid dispensing feature.

Example 5

The apparatus of Example 4, wherein the control module is operable to selectively activate the pump to provide a pulsed flow of cooling liquid through the liquid dispensing feature.

Example 6

The apparatus of Example 5, further comprising an ultrasonic transducer assembly coupled with the acoustic waveguide, wherein the control module is further operable to activate the ultrasonic transducer assembly.

Example 7

The apparatus of Example 6, wherein the control module is further operable to activate the ultrasonic transducer assembly through a first pulsed drive signal, wherein the control module is further operable to activate the pump through a second pulsed drive signal.

Example 8

The apparatus of Example 7, wherein the control module is programmed to provide pump activating pulses between ultrasonic transducer assembly driving pulses.

Example 9

The apparatus of any one or more of Examples 4 through 8, wherein the control module is operable to selectively activate the pump to provide a high pressure fluid flow and a low pressure fluid flow.

Example 10

The apparatus of any one or more of Examples 1 through 9, wherein the liquid dispensing feature comprises a valve, wherein the control module is operable to activate the valve to thereby regulate flow of cooling liquid through the liquid dispensing feature.

Example 11

The apparatus of any one or more of Examples 1 through 10, wherein the control module is configured to: (i) monitor at least one feedback condition associated with operation of the ultrasonic blade, and (ii) regulate flow of cooling liquid through the liquid dispensing feature in real time based on the at least one feedback condition.

Example 12

The apparatus of Example 11, wherein the at least one feedback condition is indicative of temperature of the ultrasonic blade.

Example 13

The apparatus of Example 12, wherein the at least one feedback condition comprises frequency slope associated with ultrasonic vibration of the ultrasonic blade.

Example 14

The apparatus of any one or more of Examples 11 through 13, wherein the control module is further configured to adjust excursion of the ultrasonic blade in real time based on the at least one feedback condition.

Example 15

The apparatus of any one or more of Examples 1 through 14, further comprising a blade reciprocating feature, wherein the blade reciprocating feature is operable to provide gross reciprocation of the ultrasonic blade relative to the body assembly.

Example 16

The apparatus of Example 15, wherein the blade reciprocating feature comprises a solenoid.

Example 17

The apparatus of any one or more of Examples 15 through 16, wherein the control module is operable to activate the blade reciprocating feature.

Example 18

An apparatus comprising: (a) a body assembly; (b) an acoustic waveguide; (c) an ultrasonic blade positioned distally relative to the body assembly, wherein the ultrasonic blade is in acoustic communication with the acoustic waveguide; (d) a liquid dispensing feature positioned distally relative to the body assembly, wherein the liquid dispensing feature is positioned adjacent to the ultrasonic blade, wherein the liquid dispensing feature is configured to deliver a flow of cooling liquid to the ultrasonic blade; and (e) a temperature sensitive valve, wherein the temperature sensitive valve is configured to regulate flow of cooling liquid through the liquid dispensing feature.

Example 19

The apparatus of Example 18, wherein the temperature sensitive valve comprises a temperature sensitive material in thermal communication with the ultrasonic blade, wherein the temperature sensitive material is configured to expand and contract based on a temperature of the ultrasonic blade, wherein the temperature sensitive valve defines an orifice, wherein the temperature sensitive material is configured to change a size of the orifice based on expansion and contraction of the temperature sensitive material.

Example 20

An apparatus comprising: (a) a body assembly; (b) an acoustic waveguide; (c) an ultrasonic blade positioned distally relative to the body assembly, wherein the ultrasonic blade is in acoustic communication with the acoustic waveguide; (d) an ultrasonic transducer assembly coupled with the acoustic waveguide; (e) a liquid dispensing feature, wherein the liquid dispensing feature is configured to deliver a flow of cooling liquid to the ultrasonic blade; (f) a blade reciprocating feature, wherein the blade reciprocating feature is operable to provide gross reciprocation of the ultrasonic blade relative to the body assembly; and (g) a control module, wherein the control module is operable to selectively activate the ultrasonic transducer assembly, wherein the control module is further operable to selectively activate the blade reciprocating feature.

VIII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an acoustic waveguide;
   (b) an ultrasonic blade in acoustic communication with the acoustic waveguide;
   (c) a liquid dispensing feature positioned adjacent to the ultrasonic blade, wherein the liquid dispensing feature is configured to deliver a flow of cooling liquid to the ultrasonic blade; and
   (d) a control module, wherein the control module is operable to regulate fluid flow through the liquid dispensing feature,
   wherein the control module is configured to direct activation of the ultrasonic blade according to a first pulsed drive signal and further direct activation of the liquid dispensing feature according to a second pulsed drive signal, wherein the first pulsed drive signal includes a plurality of first predetermined timed pulses each configured to activate the ultrasonic blade a first predetermined pulse time, wherein the second pulsed drive signal includes a plurality of second predetermined timed pulses configured to activate the liquid dispensing feature a second predetermined pulse time, and
   wherein the control module is further configured to provide the plurality of second predetermined timed pulses respectively between the plurality of first predetermined timed pulses such that the plurality of second predetermined timed pulses do not overlap with the plurality of first predetermined timed pulses during at least a portion of the first pulsed drive signal to thereby inhibit converting the cooling liquid into a mist upon contact with the ultrasonic blade for delivering the cooling liquid to a patient.

2. The apparatus of claim 1, further comprising an ultrasonic transducer assembly coupled with the acoustic waveguide, wherein the control module is further operable to activate the ultrasonic transducer assembly.

3. The apparatus of claim 1, further comprising a pump in fluid communication with the liquid dispensing feature.

4. The apparatus of claim 3, wherein the control module is operable to selectively activate the pump through the second pulsed drive signal to provide a pulsed flow of cooling liquid through the liquid dispensing feature.

5. The apparatus of claim 4, further comprising an ultrasonic transducer assembly coupled with the acoustic waveguide, wherein the control module is further operable to activate the ultrasonic transducer assembly.

6. The apparatus of claim 5, wherein the control module is further operable to activate the ultrasonic transducer assembly through the first pulsed drive signal.

7. The apparatus of claim 3, wherein the control module is operable to selectively activate the pump to provide a high pressure fluid flow and a low pressure fluid flow.

8. The apparatus of claim 1, wherein the liquid dispensing feature comprises a valve, wherein the control module is operable to activate the valve to thereby regulate flow of the cooling liquid through the liquid dispensing feature.

9. The apparatus of claim 1, wherein the control module is configured to:
   (i) monitor at least one feedback condition associated with operation of the ultrasonic blade, and
   (ii) regulate flow of the cooling liquid through the liquid dispensing feature in real time based on the at least one feedback condition.

10. The apparatus of claim 9, wherein the at least one feedback condition is indicative of a temperature of the ultrasonic blade.

11. The apparatus of claim 10, wherein the at least one feedback condition comprises a frequency slope associated with ultrasonic vibration of the ultrasonic blade.

12. The apparatus of claim 9, wherein the control module is further configured to adjust an excursion of the ultrasonic blade in real time based on the at least one feedback condition.

13. The apparatus of claim 1, wherein the liquid dispensing feature has a distal-most end, wherein the ultrasonic blade has a node and an anti-node configured to propagate vibratory motion thereon, wherein the distal-most end of the liquid dispensing feature is positioned at the node to thereby inhibit dispersing the cooling liquid laterally away from the ultrasonic blade.

14. The apparatus of claim 1, wherein the control module is configured such that the plurality of second predetermined timed pulses at least partially overlap with the plurality of first predetermined time pulses during at least another portion of the first pulsed drive signal.

15. The apparatus of claim 1, further comprising a body assembly including a fluid port and an activation member, wherein the fluid port is fluidly connected to the liquid dispensing feature and configured to receive the cooling liquid, wherein the activation member is operatively connected to the control module and configured to be selectively manipulated to selectively direct the control module to activate the ultrasonic blade and the liquid dispensing feature, and wherein the activation member is positioned between the fluid port and the ultrasonic blade.

16. The apparatus of claim 1, wherein the ultrasonic blade defines an oblong transverse opening therethrough.

17. The apparatus of claim 1, further comprising a body assembly, wherein the ultrasonic blade is positioned distally relative to the body assembly, and wherein the liquid dispensing feature is positioned distally relative to the body assembly.

18. The apparatus of claim 1, wherein the control module is further configured to provide the plurality of second predetermined timed pulses between the plurality of first predetermined timed pulses such that the plurality of second predetermined timed pulses do not overlap with the plurality of first predetermined timed pulses during all of the first pulsed drive signal.

19. A method of delivering a flow of cooling liquid to a patient with a surgical instrument, wherein the surgical instrument includes (a) an acoustic waveguide; (b) an ultrasonic blade in acoustic communication with the acoustic waveguide; (c) a liquid dispensing feature positioned adjacent to the ultrasonic blade, wherein the liquid dispensing feature is configured to deliver the flow of cooling liquid to the ultrasonic blade; and (d) a control module, wherein the control module is operable to regulate fluid flow through the liquid dispensing feature, wherein the control module is configured to direct activation of the ultrasonic blade according to a first pulsed drive signal and further direct activation of the liquid dispensing feature according to a second pulsed drive signal, wherein the first pulsed drive signal includes a plurality of first predetermined timed pulses each configured to activate the ultrasonic blade a first predetermined pulse time, wherein the second pulsed drive signal includes a plurality of second predetermined timed pulses configured to activate the liquid dispensing feature a second predetermined pulse time, and wherein the control module is further configured to provide the plurality of second predetermined timed pulses respectively between the plurality of first predetermined timed pulses such that the plurality of second predetermined timed pulses do not overlap with the plurality of first predetermined timed pulses during at least a portion of the first pulsed drive signal to thereby inhibit converting the cooling liquid into a mist upon contact with the ultrasonic blade for delivering the cooling liquid to the patient, the method comprising: (a) directing activation of the ultrasonic blade according to the first pulsed drive signal via the control module; (b) directing activation of the liquid dispensing feature according to the second pulsed drive signal via the control module; (c) providing the liquid dispensing feature activating second pulsed drive signal between the ultrasonic blade driving first pulsed drive signal to thereby inhibit conversion of the cooling liquid into the mist upon contact with the ultrasonic blade; and (d) delivering the cooling liquid to the patient.

\* \* \* \* \*